(12) United States Patent
Rhodes et al.

(10) Patent No.: US 10,481,142 B2
(45) Date of Patent: Nov. 19, 2019

(54) SENSOR SYSTEM FOR DETERMINING SOIL CHARACTERISTICS

(71) Applicant: Deere & Company, Moline, IL (US)

(72) Inventors: Michael Rhodes, Richfield, MN (US); Nikolai Tevs, Daytona Beach Shores, FL (US); Jeffrey S Puhalla, Hawley, MN (US)

(73) Assignee: DEERE & COMPANY, Moline, IL (US)

(*) Notice: Subject to any disclaimer, the term of this patent is extended or adjusted under 35 U.S.C. 154(b) by 222 days.

(21) Appl. No.: 15/605,251

(22) Filed: May 25, 2017

(65) Prior Publication Data

US 2018/0340845 A1 Nov. 29, 2018

(51) Int. Cl.
| | |
|---|---|
| *G01N 33/24* | (2006.01) |
| *A01B 61/00* | (2006.01) |
| *A01B 76/00* | (2006.01) |
| *A01B 79/02* | (2006.01) |
| *A01B 5/04* | (2006.01) |
| *A01C 5/06* | (2006.01) |
| *G01L 1/00* | (2006.01) |
| *G01N 3/40* | (2006.01) |

(52) U.S. Cl.
CPC .............. *G01N 33/24* (2013.01); *A01B 5/04* (2013.01); *A01B 61/00* (2013.01); *A01B 76/00* (2013.01); *A01B 79/02* (2013.01); *A01C 5/064* (2013.01); *G01L 1/005* (2013.01); *G01N 3/40* (2013.01); *G01N 2033/245* (2013.01)

(58) Field of Classification Search
CPC .. G01N 3/20; G01N 3/24; G01N 3/40; G01N 33/24; G01N 2033/245; G01L 1/005

USPC ........... 73/84, 781, 788, 818, 841, 843, 849
See application file for complete search history.

(56) References Cited

U.S. PATENT DOCUMENTS

| | | | |
|---|---|---|---|
| 5,490,427 A | 2/1996 | Yee et al. | |
| 6,701,857 B1 * | 3/2004 | Jensen | A01B 63/32 111/200 |
| 7,926,362 B2 | 4/2011 | Andersson et al. | |
| 8,561,472 B2 | 10/2013 | Sauder et al. | |
| 8,738,244 B2 | 5/2014 | Lenz et al. | |
| 8,827,001 B2 | 9/2014 | Wendte et al. | |

(Continued)

FOREIGN PATENT DOCUMENTS

| | | |
|---|---|---|
| EP | 3150045 A1 | 4/2017 |
| WO | 03023396 A2 | 3/2003 |

OTHER PUBLICATIONS

European Search Report issued in counterpart application No. 18169355.7 dated Oct. 16, 2018. (7 pages).

*Primary Examiner* — Benjamin R Schmitt (57) ABSTRACT

A sensor system for determining soil characteristics is disclosed herein. The sensor system includes a ground engaging device for coupling to an agricultural implement. The ground engaging device includes at least one disc member having an aperture and an elongate shaft extending through the aperture. A first sensor unit is arranged on a sensing surface of the disc member and is configured to measure forces acting on the disc member. A second sensor unit is arranged on the elongate shaft and is configured to measure forces acting on the shaft. A processor is communicatively coupled to each of the first and second sensor units. The processor is configured to generate an output signal indicative of a soil characteristic based on the forces measured.

16 Claims, 7 Drawing Sheets

(56) References Cited

U.S. PATENT DOCUMENTS

2004/0162680 A1* 8/2004 Shiraishi ............ B60G 17/0195
702/43
2012/0125244 A1 5/2012 Beaujot
2014/0041563 A1 2/2014 Henry et al.

* cited by examiner

SENSOR SYSTEM FOR DETERMINING SOIL CHARACTERISTICS

TECHNICAL FIELD

The present disclosure generally relates to a sensor system that utilizes force measurements to determine soil characteristics.

BACKGROUND

In farming applications, it is often desirable to know certain characteristics of the soil in real-time as the farmer is performing a task such as planting or tilling. Such characteristics may include soil hardness, soil strength, soil compactness, temperature, and trench depth; each of which can be of extreme importance in ensuring optimal yields. For example, inadequate soil conditions may adversely affect crop production, thereby leading to decreased yields. Additionally, because agricultural implements or other apparatuses are designed for specific types of soil conditions, improper soil conditions could lead to premature damage or failure of various machine components.

Drawbacks to some prior art approaches, however, include increased costs or decreased sensor resolution. As such, there is a need in the art for a sensor system that provides increased resolution at lower costs.

SUMMARY

In accordance with one embodiment, a sensor system for determining soil characteristics, the sensor system comprises a ground engaging device coupled to an agricultural implement, where the ground engaging device comprises at least one disc member having an aperture and an elongate shaft extending through the aperture. A first sensor unit is arranged on a sensing surface of the disc member, wherein the first sensor unit is configured to measure forces acting on the disc member, and wherein the forces comprise at least one first force acting in a first direction and at least one second force acting in a second direction. A second sensor unit is arranged on the elongate shaft, wherein the second sensor unit is configured to measure forces acting on the shaft, and wherein the forces comprise at least one third force acting in a third direction and at least one fourth force acting in a fourth direction. A processor is communicatively coupled to each of the first and second sensor units. The processor is configured to generate an output signal indicative of a soil characteristic based on the forces measured in the first and second directions.

BRIEF DESCRIPTION OF THE DRAWINGS

Like reference numerals are used to indicate like elements throughout the several figures.

DETAILED DESCRIPTION

Figure 1:
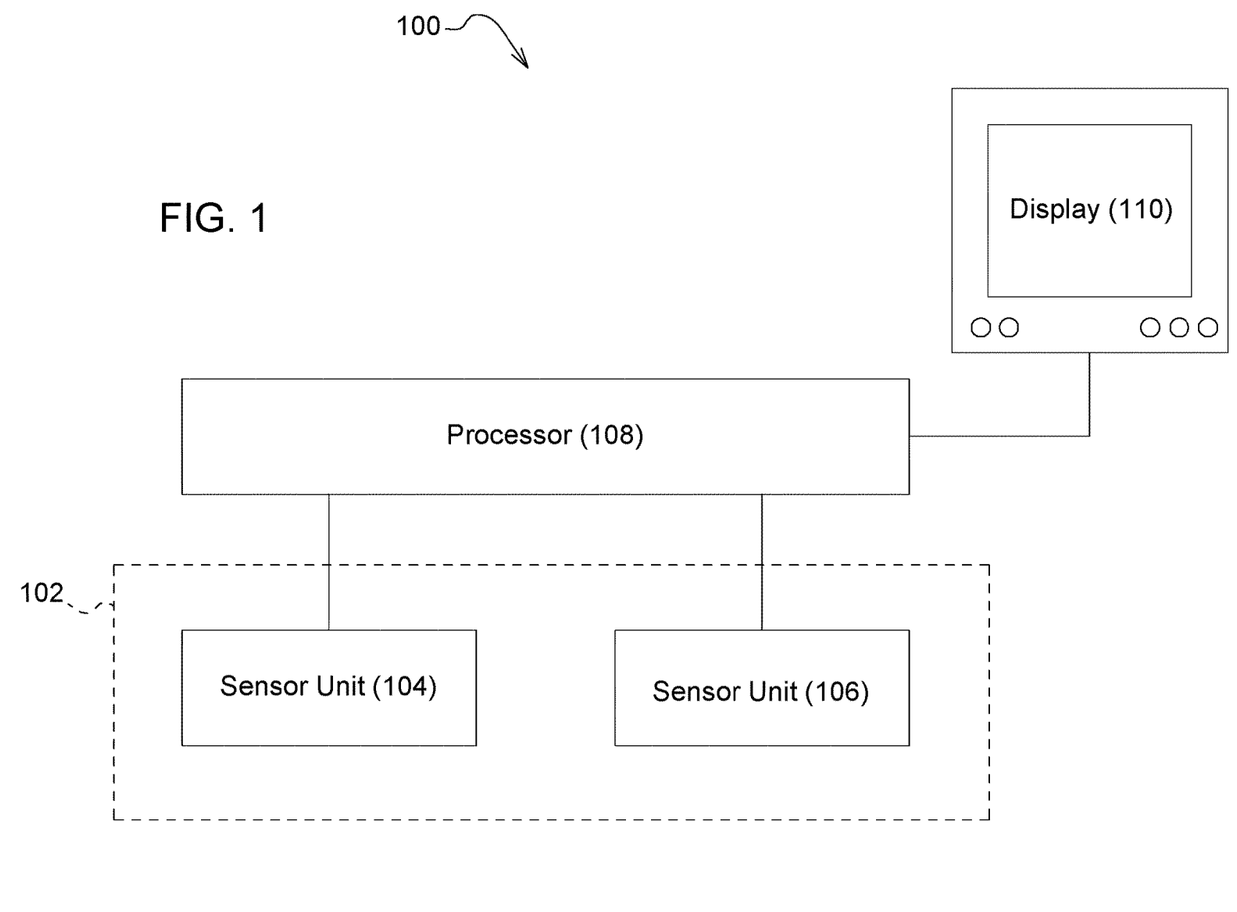
FIG. 1 is a block diagram of a sensor system according to an embodiment.
Figure 2:
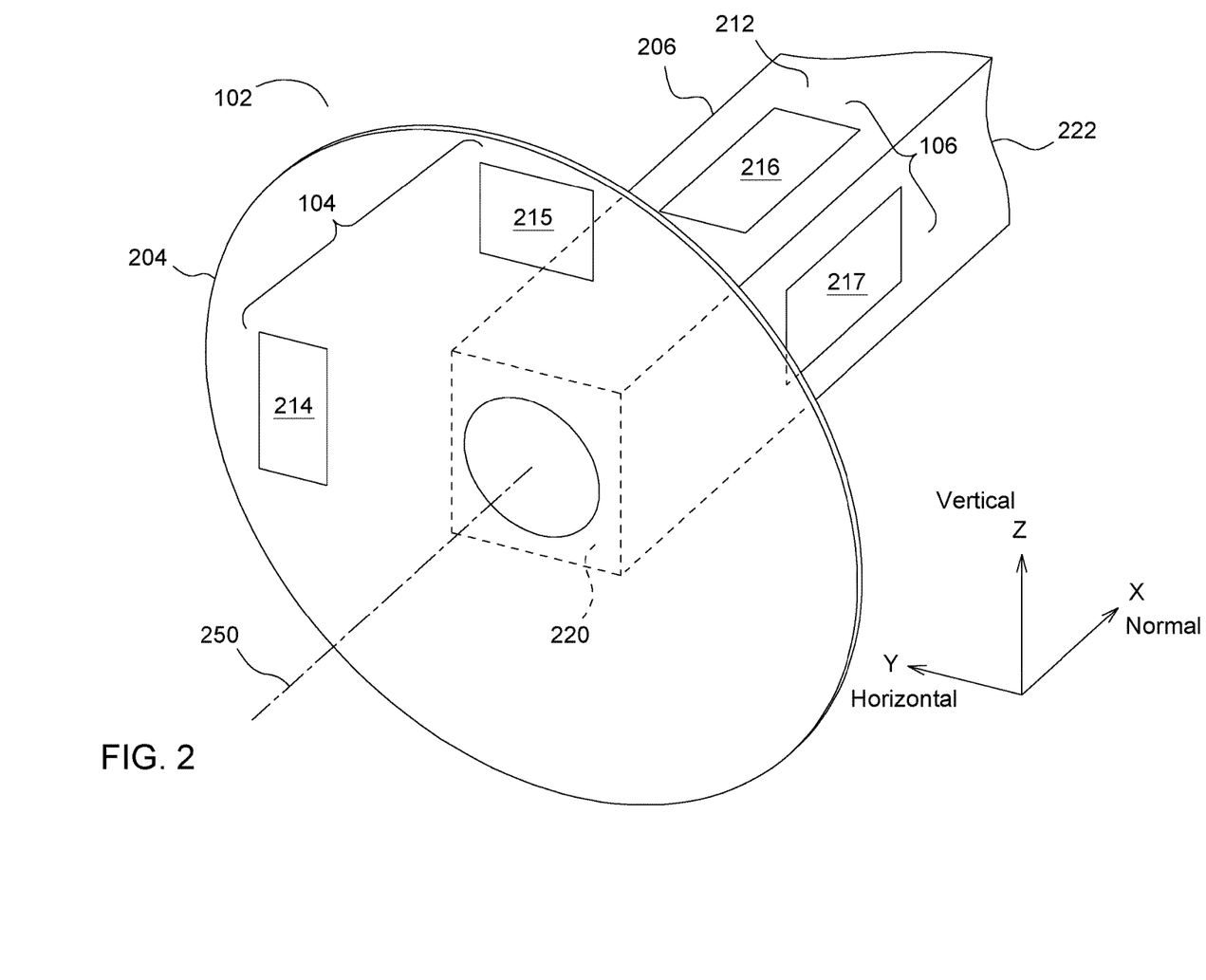
FIG. 2 is a perspective view of a ground engaging device employed in the sensor system of FIG. 1 according to an embodiment.

For purposes of clarity, the present disclosure will be described as being implemented in a planter unit. It should be noted, however, that the present disclosure may also be employed in a variety of planting and/or soil preparation applications to include, but not limited to, tillage, seeding, and others. Referring to FIGS. 1-2, a sensor system 100 for determining soil characteristics is shown according to an embodiment.

In embodiments, the sensor system 100 can comprise at least two sensor units 104, 106 communicatively coupled to an electronic data processor 108 and arranged on a ground engaging device 102. As illustrated in FIG. 2, the ground engaging device 102 can be adapted for coupling to an agricultural implement (e.g., planter unit 400 in FIG. 5A) and can include at least one disc member 204 coupled to an axle shaft 206 for rotation with respect to the axle or for rotation with the axle. Although the axle is illustrated with a rectangular cross section in FIG. 2, in other embodiments the axle shaft may have a substantially circular cross section or a cylindrical portion to interface with a radial bearing near the disc member 204. The disc member 204 can comprise an opener disc or another wheel-like structure that is arranged to rotationally engage with or penetrate the surrounding soil as the agricultural implement is moved throughout a field. The axle shaft 206 may include an elongate structure 210 having a plurality of outer surfaces 212 that extend along a center axis 250 between a first and a second end 220, 222. In one embodiment, the first end 220 is affixed to the disc member 204 and the second end 222 is affixed to a frame of the agricultural implement if the disc member 204 is configured not to rotate. However, in another embodiment, the first end 220 interfaces the disc member 204 with a radial bearing to allow the disc member 204 and the shaft 206 to rotate with respect to one another.

Figure 3:
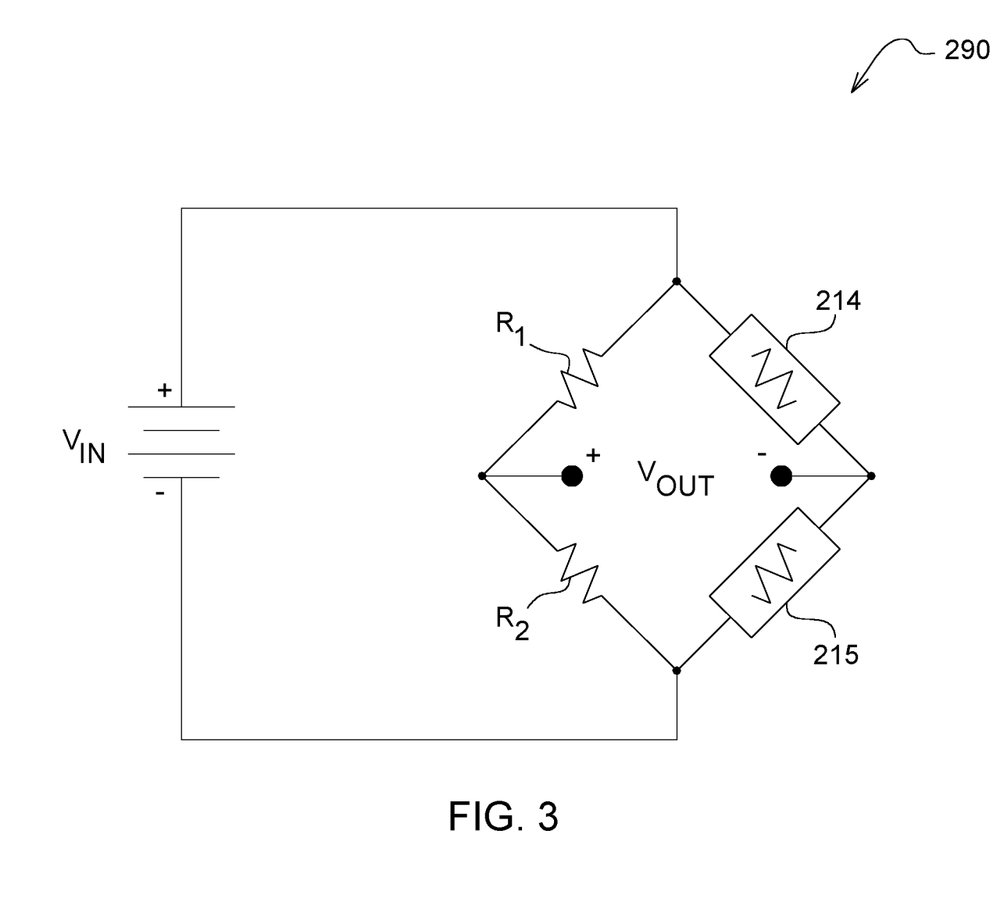
FIG. 3 is a schematic illustration of a sensor unit according to an embodiment.

As illustrated in FIG. 2 and FIG. 3, sensor units 104, 106 can respectively comprise one or more sensor elements, such as sensor elements 214-217, disposed on a surface of the disc member 204 and/or the axle shaft 206. Each sensor unit 104, 106 may be individually or collectively powered utilizing various energy sources such as, e.g., harvested energy sources, AC power sources, or DC power sources arranged internal or external to the sensor units 104, 106.

In various embodiments, sensor elements 214-217 may comprise strain gauges or other suitable load sensing devices specific to application requirements. For example, in some embodiments, each set of sensor elements (i.e., sensor elements 214, 215 and sensor elements 216, 217) can include at least two strain gauges (e.g., piezoelectric or piezoresistive sensors) angularly displaced in spaced relation (e.g., ~90 degree angular displacement) from one another with respect to the center axis 250. Such an arrangement allows for the measurement of the forces (e.g., torsional forces) applied to the disc member 204 or axle shaft 206 under varying conditions. As depicted in FIG. 2, coordinates x, y, z, define the directions in which applicable forces may be applied. The Z axis will be in the vertical direction, the Y axis will be in the horizontal direction, and the X axis will be in the direction normal to the plane of the page. For example, the first set of sensor elements 214, 215 can be disposed on an outer surface of disc member 204 and arranged to detect bending strains due to laterally applied external forces in the xz-plane. Similarly, the second set of sensor elements 216, 217 can be disposed on an outer surface of the axle shaft 206 and arranged to detect shear strains due to axially applied external forces in the yz-plane.

The electronic data processor 108 may include a microprocessor, a microcontroller, a digital signal processor, a programmable logic controller, or other suitable computing devices capable of processing data signals generated by sensor units 104, 106. In some embodiments, the processed data may be monitored on a graphical user interface, such as a display 110, which can be arranged in a cab of an operator vehicle to provide real-time view of such information. In other embodiments, the processed data may be stored in a memory, which may include, but is not limited to, random access memory (RAM), read only memory (ROM), optical data storage, dynamic data storage, and/or combinations thereof.

With respect to FIGS. 1-2, it will be appreciated by those skilled in the art that FIGS. 1-2 are not drawn to scale and are for illustrative purposes only. Notably, the size, dimensions, structural layout, and quantity of the various components can and will vary in other embodiments. For example, in some embodiments, sensor system 100 may comprise three or more sensor units 104, 106 arranged on ground engaging device 102 to provide increased measurement accuracy. In other embodiments, sensor system 100 may further comprise angle sensors or other position related sensors which are used to determine the rotational position of the disc member 204. Additionally, although in embodiments discussed herein sensor units 104, 106 will include force sensors, it should be noted that other suitable sensing devices may be employed. For example, in other embodiments, sensor units 104, 106 may include, load sensors, torque sensors, inductive sensors, capacitive sensors, or combinations thereof.

Referring now to FIG. 3, a schematic illustration of the sensor units 104, 106 as discussed with reference to FIGS. 1 and 2 is shown according to an embodiment. As depicted, each sensor unit 104, 106 can include one or more sensor elements (i.e., sensor elements 214, 215 and sensor elements 216, 217) electrically coupled in series to form half-bridge circuit arrangements. Each pair of sensor elements (sensor elements 214, 215 and sensor elements 216, 217) can comprise resistive elements that are arranged to form branches of a Wheatstone bridge along with resistors R1 and R2, which are balancing resistors having fixed resistances included for measurement purposes. In FIG. 3, sensor elements 214, 215 and 216, 217 are shown as including half bridge configurations, however, it should be noted that such a configuration is for exemplary purposes only and other suitable configurations may be employed. For example, in other embodiments, sensor units 104, 106 may comprise fewer or more sensor elements 214-217 that may also be arranged in full bridge configurations.

Referring now back to FIG. 2, sensor elements 214, 215 and 216, 217 are arranged so as to measure bending and shear forces acting on the disc member 204 and axle shaft 206. For example, as the resistances of R2 and sensor element 214 increase there will be a simultaneous decrease in the measured resistances of R1 and sensor element 215 corresponding to changes in applied strains and forces can be measured. In other words, in such an arrangement, when no external force is applied, sensor elements 214-217 will have equal resistances and each bridge circuit will be balanced. However, once an external force is applied in either a lateral or longitudinal direction, bending and shear strains will be experienced by the disc member 204 and axle shaft 206 correspondingly. For example, upon application of a bending force, a corresponding moment is developed in the disc member 204, which thereby causes the disc member 204 to bend. This in turn is reflected in the output signal Vout of the bridge circuit 290 when the input signal Vin is applied. The output voltage Vout of the bridge circuit 290 will be proportional to the measured bending force applied to the disc member 204, or similarly, in the case of the axle shaft, the shear force applied to the axle shaft 206. In some embodiments, sensor system 100 may further comprise a signal conditioner that is configured to apply conditioning and/or amplification circuitry (e.g., a differential amplifier, A/D converter or filter) to the output signal Vout prior to processing by the electronic data processor 108.

Figure 4:
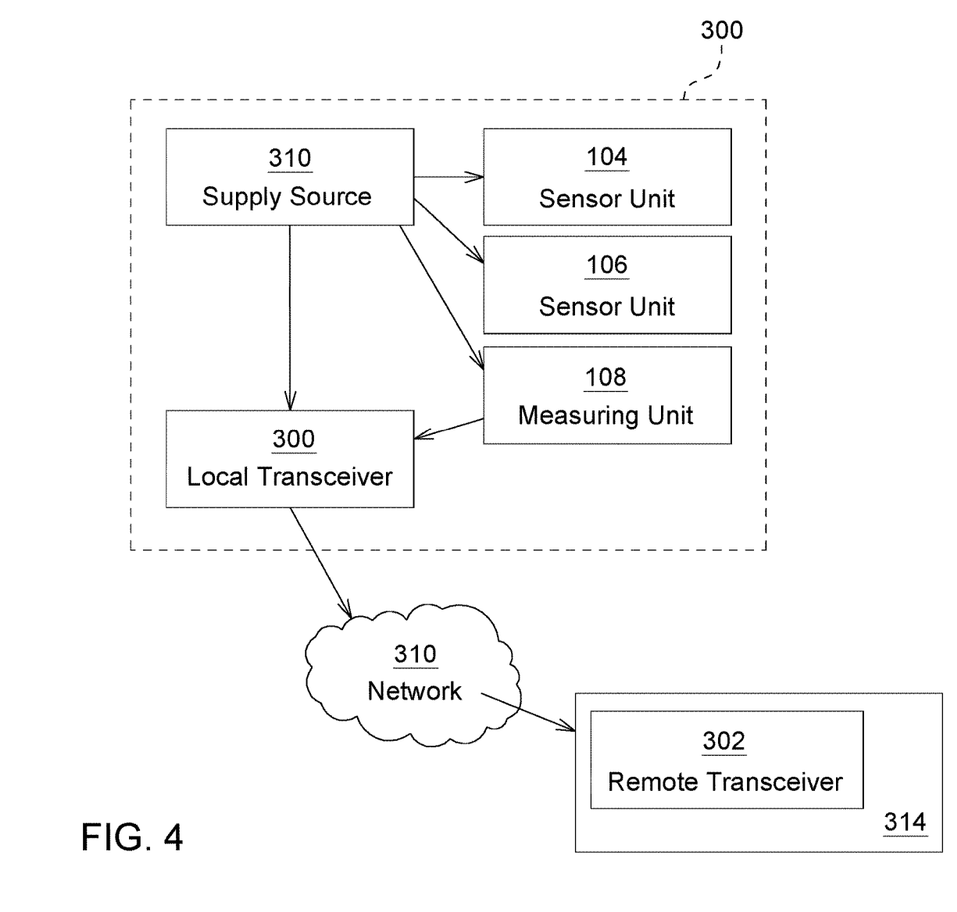
FIG. 4 is a block diagram of a sensor system according to an embodiment.

Referring now to FIG. 4, in some embodiments, sensor system 100 may further comprise a local transceiver 300 in communication with the sensor units 104, 106 and electronic data processor 108. The local transceiver 300 may be configured to transmit and receive data transmissions to and from one or more remote transceivers 302 wirelessly over network 310, which may include the Internet. For example, as illustrated, the local transceiver 300 can transmit sensor data from measuring unit 308 to a remote processing unit 314 having a remote transceiver 302. The transceivers 300, 302 may be compatible with IEEE 802.11 and/or Bluetooth protocols and access to network 310 may be provided, for example, via a local area network (LAN), wide area network (WAN), wireless area network (WLAN), or suitable communication network. In some embodiments, the remote processing unit 314 can perform the functions described above with respect to the electronic data processor 108. In other embodiments, the remote processing unit 314 may be configured to perform additional processing or data analysis that is made available to a secondary user or operator.

Figure 5A:
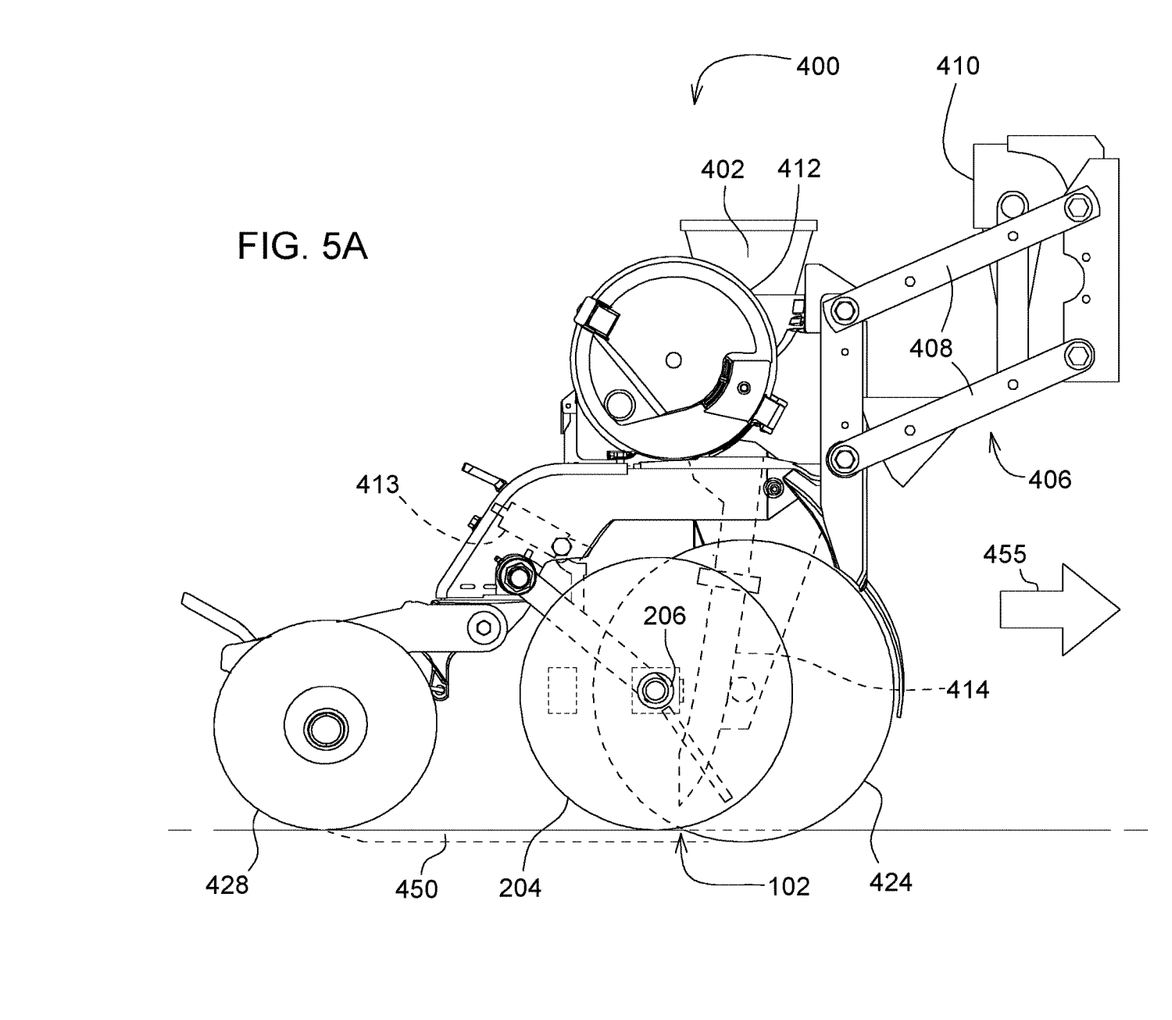
FIG. 5A is a side view of an agricultural implement in which the sensor system of FIG. 1 is arranged according to an embodiment.

In FIG. 5A, a planter unit 400 in which sensor system 100 is incorporated is shown according to an embodiment. The planter unit 400 can comprise a hopper 402 arranged in a generally upright position that is mounted to a frame 404. A parallel arm arrangement 406 comprising linkages 408 and an actuation device 410 can be mounted to frame 404 in a cantilever-like configuration such that it extends outwardly and away from frame 404. In some embodiments, actuation device 410 can be coupled to at least one of linkages 408 and can include mechanical, pneumatic, hydraulic, or other suitable actuators to apply lift and/or downforce to planter unit 400. A metering unit 412 having a generally circular configuration can be arranged beneath hopper 402 and can be configured to distribute seeds received from hopper 402 into a seed tube 414. The seed tube 414 directs the seeds received from the metering unit 412 to a soil opening 450 formed in the ground by the disc member 204.

As previously discussed with reference to FIG. 1, the ground engaging device 102 can comprise at least one disc member 204 operably coupled to the axle shaft 206, with the disc member 204 being arranged to form the soil opening 450 at a predetermined penetration depth upon engagement with the soil. As depicted, the axle shaft 206 may be coupled to a frame of the planter unit 400. At least two gauge wheels 424 are mounted proximate the disc member 204 such that the soil penetration depth of the disc member 204 is regulated by gauge wheels 424. For example, the actuation device 410 operates to apply a downforce to planter unit 400, which in turn applies appropriate downforces to each of the ground engaging devices (i.e., gauge wheels 424 and disc member 204) mounted to planter unit 400. Once the devices are lowered, a gauge wheel adjustment mechanism 413 enables the vertical position of the gauge wheels 424 to be adjusted relative to the disc member 204, which establishes the depth at which the disc member 204 is inserted into the soil (i.e., the depth of the soil opening 450). In some embodiments, the adjustment mechanism 413 may be manually adjusted via a vehicle operator, whereas, in other embodiments, the adjustment mechanism 413 may be adjusted via a closed loop control algorithm implemented by the electronic data processor 108. A closing wheel assembly 428 can be arranged following the disc member 204 and gauge wheels 424, and is operable to close the soil opening 450 formed by disc member 204.

Figure 5B:
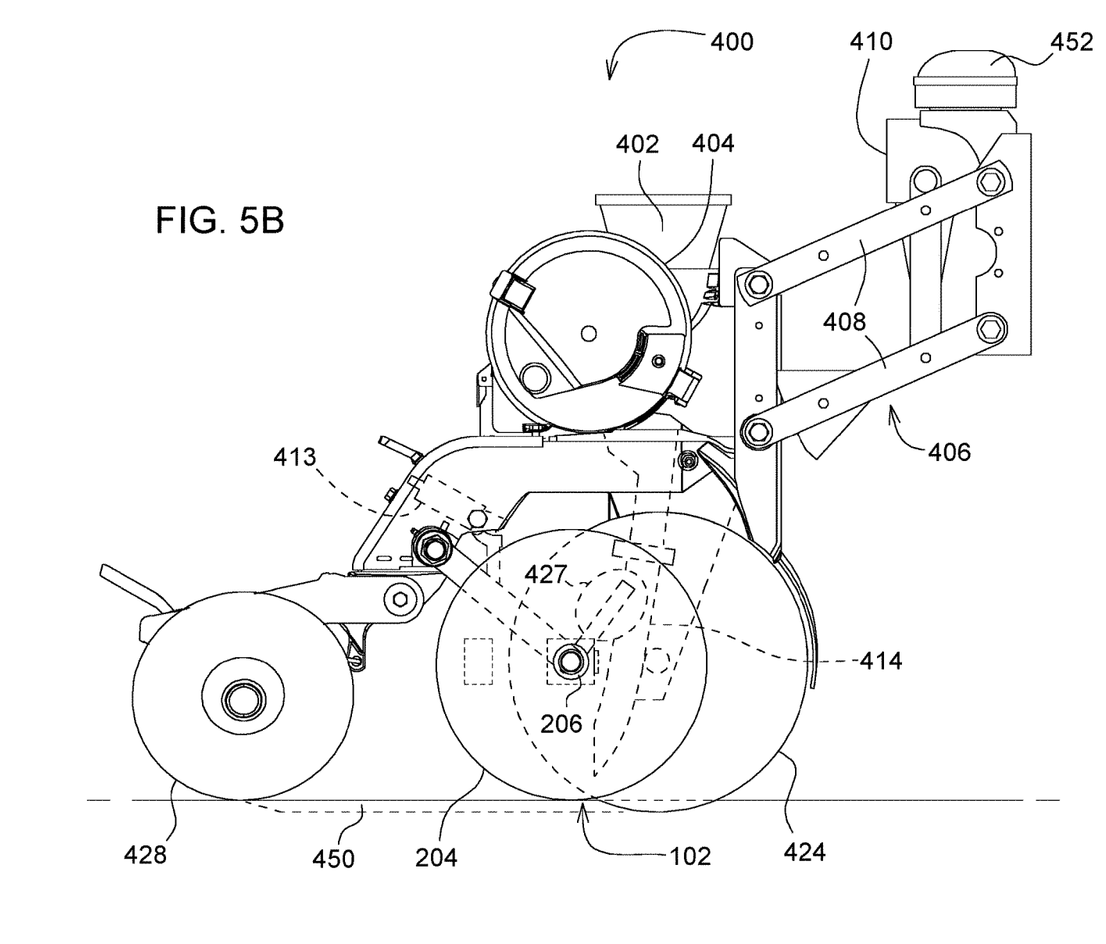
FIG. 5B is a side view of an agricultural implement in which the sensor system of FIG. 1 is arranged according to an embodiment.

In some embodiments, referring now to FIG. 5B, planter unit 400 may further comprise a location-determining receiver 452, such as a satellite navigation receiver, that is mounted to the planter unit 400 and configured to provide field location data. In other embodiments, planter unit 400 may also comprise a scraper unit 427 mechanically coupled to the axle shaft 206 that is configured to remove excess dirt or other residual material buildup from the disc member 204. For example, in muddy soil conditions, mud or other similar materials may adhere to the engaging member 110, thereby decreasing sensing accuracy of sensor unit 104. To prevent such interference, scraper unit 427 can be mounted to engage with a forward surface of the disc member 204 as it rotationally engages with the soil to remove any excess material.

Figure 6:
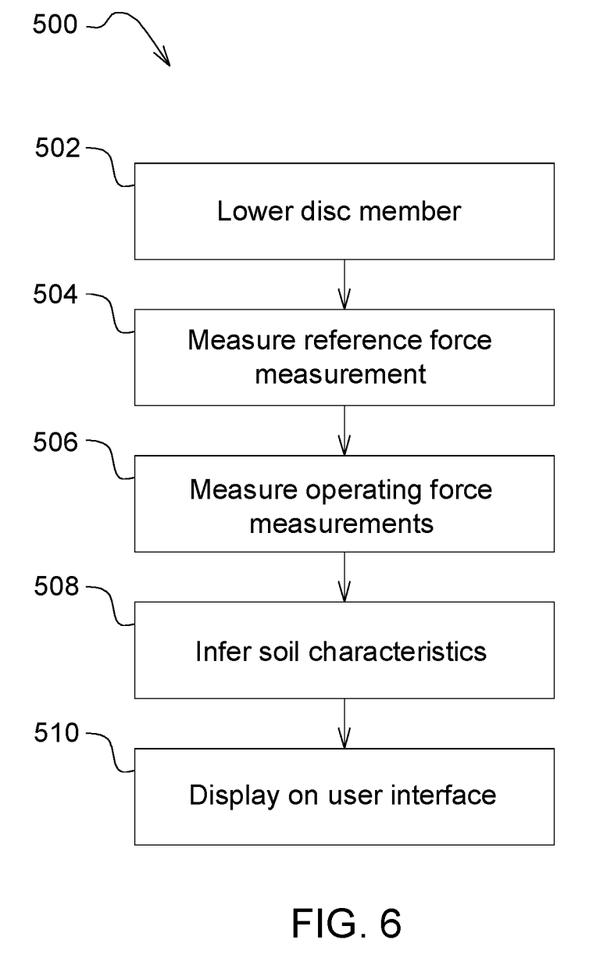
FIG. 6 is a flow diagram of a method for obtaining a gradient of soil properties utilizing the sensing wheel system of the present invention.

In FIG. 6, a flow diagram of a method 500 for carrying out the present disclosure is shown. At 502, an operator may input a command through a user interface of display 110 to enable adjustment of the vertical position (i.e., raising or lowering) of the gauge wheels 424, which, in turn, adjusts the vertical position of the disc member 104. This establishes the penetration depth to which the disc member 204 is inserted into the soil, i.e., the depth of the soil opening 450. Next at 504, and prior to operation, a reference force measurement is taken by each of sensor units 104, 106 while the disc member 204 is positioned in the soil and stored in memory 122 as an indication of ideal soil characteristics.

In operation, and as planter unit 400 is moving throughout a field, a plurality of operating force measurements are taken by sensor units 104, 106 and transmitted to the electronic data processor 108 at 506. For example, as disc member 204 rotates throughout the soil, the plurality of operating force measurements are taken and compared against the reference force measurement as various soil conditions are encountered such as increased soil hardness or compaction. For example, as hardened soil conditions are encountered, shear strains experienced by the axle shaft 206 will increase as it becomes increasingly difficult for the disc member 204 to penetrate the soil. Similarly, as the soil becomes more compact, the disc member 204 will experience increased bending strains resulting from surface deformations (i.e., bending) of the disc member 204 caused by the externally applied forces of the soil. Such changes will be reflected in the output signal Vout of the bridge circuit as discussed with reference to FIG. 3 and processed by the electronic data processor 108. For example, once the output signal Vout is received, the electronic data processor 108 will correlate the output signal Vout to soil characteristic data (e.g., soil hardness, soil compaction, soil strength) contained in a look-up table that is stored in memory of or dynamically generated by the electronic data processor 108. Next at 510, a profile of the inferred soil characteristics may be displayed on display 110.

Without in any way limiting the scope, interpretation, or application of the claims appearing below, a technical effect of one or more of the example embodiments disclosed herein is sensor system for determining soil characteristics. While the present disclosure has been illustrated and described in detail in the drawings and foregoing description, such illustration and description is not restrictive in character, it being understood that illustrative embodiment(s) have been shown and described and that all changes and modifications that come within the spirit of the present disclosure are desired to be protected. Alternative embodiments of the present disclosure may not include all of the features described yet still benefit from at least some of the advantages of such features. Those of ordinary skill in the art may devise their own implementations that incorporate one or more of the features of the present disclosure and fall within the spirit and scope of the appended claims.

What is claimed is:

1. A sensor system for determining soil characteristics, the sensor system comprising:
    a ground-engaging device coupled to an agricultural implement, the ground engaging device comprising at least one disc member having an aperture and an elongate shaft extending through the aperture;
    a first sensor unit disposed on the disc member, wherein the first sensor unit is configured to measure a first force acting on the disc member in a first direction;
    a second sensor unit disposed on the elongate shaft, wherein the second sensor unit is configured to measure a second force acting on the elongate shaft in a second direction; and
    an electronic data processor communicatively coupled to each of the first and second sensor units, the electronic data processor being configured to inferentially determine a soil characteristic based on the first and second force measurements.

2. The sensor system of claim 1, wherein the first and second sensor units respectively comprise at least two sensor elements angularly displaced relative to one another by approximately 90-degrees.

3. The sensor system of claim 2, wherein the at least two sensor elements are arranged in half bridge or full bridge circuit arrangements.

4. The system of claim 1, wherein the first direction is generally perpendicular to the second direction.

5. The sensor system of claim 1, wherein the first or second force measurement comprises at least one of a shear force or a bending force.

6. The sensor system of claim 1, wherein the disc member comprises at least one of an opener disc, a tillage wheel, or a grain drill.

7. The sensor system of claim 1 further comprising three or more sensor units.

8. The sensor system of claim 1, wherein the determined soil characteristic comprises one more of the following: soil hardness, soil strength, soil compaction.

9. The sensor system of claim 1 further comprising a satellite navigation receiver for determining each position of the first and second sensor units and its associated respective measurements.

10. The sensor system of claim 1 further comprising a look-up table stored in a memory of the electronic data processor.

11. A sensor system for determining soil characteristics, the sensor system comprising:
- a ground engaging device coupled to an agricultural implement, the ground engaging device comprising at least one disc member having an aperture and an elongate shaft extending through the aperture;
- a first sensor unit disposed on the disc member, wherein the first sensor unit is configured to measure a first force acting on the disc member in a first direction;
- a second sensor unit disposed on the elongate shaft, wherein the second sensor unit is configured to measure a second force acting on the elongate shaft in a second direction;
- an electronic data processor communicatively coupled to each of the first and second sensor units, the electronic data processor being configured to determine a soil characteristic based on the first and second force measurements; and
- a satellite navigation receiver for determining a position of each of the measured forces.

12. A method for determining soil characteristics, the method comprising:
- providing a first and a second sensor unit disposed on a disc member of a ground engaging device;
- detecting a first force acting on the disc member of the ground engaging device in a first direction utilizing the first sensor unit;
- detecting a second force acting on an elongate shaft of the disc member of the ground engaging device in a second direction utilizing the second sensor unit; and
- determining a soil characteristic inferentially based on a magnitude of the first and second forces.

13. The method of claim 12, wherein the first force includes a bending force acting in a first direction and the second force includes a shear force acting in a second direction.

14. The method of claim 13, wherein the first direction is orthogonal to the second direction.

15. The method of claim 12, wherein determining the soil characteristic comprises correlating at least one of the first or second detected forces to a corresponding data value in a look-up table and inferring the soil characteristic based on the correlation.

16. The method of claim 12, wherein the at least one soil characteristic is displayed on a graphical user interface of a display.

* * * * *